United States Patent
Jones et al.

(10) Patent No.: US 6,623,463 B2
(45) Date of Patent: Sep. 23, 2003

(54) PUSH TO SET VACUUM SYSTEM

(75) Inventors: Thomas C. Jones, Columbia, MD (US); David A. Gloyd, Columbia, MD (US)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 09/859,628

(22) Filed: May 17, 2001

(65) Prior Publication Data

US 2002/0173705 A1 Nov. 21, 2002

(51) Int. Cl.[7] .............................. A61M 1/00; F16K 7/04
(52) U.S. Cl. ........................... 604/319; 251/7; 604/542
(58) Field of Search ................................ 604/319, 320, 604/542; 251/120, 121, 7; 433/95

(56) References Cited

U.S. PATENT DOCUMENTS

| | | | |
|---|---|---|---|
| 2,849,891 A | | 9/1958 | Mills |
| 3,351,090 A | * | 11/1967 | Brown et al. |
| 3,361,160 A | * | 1/1968 | Alper |
| 3,998,227 A | * | 12/1976 | Holbrook et al. ........ 137/556.6 |
| 4,164,239 A | * | 8/1979 | DeCesare .................... 137/553 |
| 4,174,733 A | | 11/1979 | Eidsmore et al. |
| 4,782,854 A | * | 11/1988 | Rozek .................... 137/315.04 |
| 4,787,416 A | | 11/1988 | Chuang |
| 4,990,137 A | * | 2/1991 | Graham ...................... 604/319 |
| 5,141,504 A | * | 8/1992 | Herweck et al. ............ 604/317 |
| 5,722,949 A | | 3/1998 | Sanese |
| 5,807,358 A | * | 9/1998 | Herweck et al. ............ 604/320 |
| 5,814,004 A | * | 9/1998 | Tamari ......................... 251/10 |

* cited by examiner

*Primary Examiner*—Alfred Basichas
(74) *Attorney, Agent, or Firm*—Roger M. Rathbun

(57) ABSTRACT

A vacuum system for applying vacuum to the body cavity of a patient where a flow switch is provided that is located upstream of a vacuum regulator that can be adjusted to establish the level of vacuum desired to be applied to the patient. The flow switch provides an easy device for the caregiver to activate to fully and positively occlude the vacuum line to the patient. In one embodiment, the flow switch is constructed integral with a regulator having an rotatable actuator having a knob that is rotated to adjust the level of vacuum to the patient such the a caregiver can simply push the actuator knob inwardly to occlude the flow in the patient line and thereafter rotate the actuator knob to establish the desired level of vacuum to the patient.

16 Claims, 4 Drawing Sheets

PUSH TO SET VACUUM SYSTEM

BACKGROUND

The present invention relates to a vacuum system that can be used to withdraw fluids from a patient, and, more particularly, to a vacuum system that has a shut off mechanism that is operable by the user to occlude the vacuum line to the patient in order to more accurately and positively establish the level of vacuum to be applied to the patient.

There are in use today, considerable uses of a vacuum systems that carry out the withdrawal of fluids from a patient cavity as well as other medical uses in a hospital for such vacuum withdrawal systems. In general, after many surgical operations, there is a need to remove certain fluids from a patient and, to that end, most hospitals normally have a pipeline supply or a source of vacuum to the patient rooms so that there is a source of vacuum present on site for use with a patient. Thus, it is relatively convenient for the hospital to simply attach a vacuum regulator to that source of vacuum in the patient room and have a regulated source of vacuum that can be established by the caregiver at the particular level of vacuum that is desired to be applied to the patient. Additionally, of course, from time to time, it is necessary for that caregiver to change the level of the vacuum applied to the patient by resetting the regulator.

As other components of typical vacuum systems, there is provided a collection container that receives and collects the quantity of fluid from the patient and that container is connected to a cannula or catheter that is, in turn, actually introduced into the particular patient cavity from which the fluids are desired to be withdrawn.

One of the present problems in such vacuum systems, however, is in determining an accurate level of vacuum by adjusting the vacuum regulator. At the present, the caregiver can directly control the vacuum regulator by the rotation of an actuator or control knob on the vacuum regulator while at the same time, visually observe a vacuum gauge to adjust and reset the level of vacuum to the desired level. In present vacuum systems, however, as long as there is a flow in the vacuum system, the setting of the vacuum regulator by a visual observation of the vacuum gauge can cause an inaccuracy, as it is important for the vacuum system to be at "no flow" conditions in order to obtain accurate readings of the maximum level of vacuum that can be applied to the patient on the vacuum gauge.

Thus, as the current systems are used, it is incumbent on the caregiver to somehow occlude the vacuum line upstream of the vacuum regulator, that is, in the vacuum line that extends from the vacuum regulator to the patient while simultaneously observing the vacuum gauge and adjusting the vacuum regulator to achieve the particular desired vacuum level.

In order to presently occlude the vacuum line to the patient, the caregiver normally will pinch the flexible vacuum line leading to the patient while, of course, at the same time, trying to read the level of the vacuum by means of the vacuum gauge and while simultaneously rotating the vacuum regulator actuator knob to set that vacuum level at the desired value.

As such, there are likely to be instances where the caregiver simply does not physically pinch the vacuum line sufficiently hard to fully occlude that line or, alternatively, the caregiver may totally omit the step of carrying out the occlusion of that vacuum line. In either event, as long as there is some flow in the vacuum line, that is, there is a flow through the regulator, the caregiver will be setting the regulator to a desired vacuum level that will actually be a lower than the potential vacuum that can reach the patient. Therefore, if the caregiver sets a desired vacuum level where there is some flow and, if the vacuum line is later fully occluded, the patient will actually experience a vacuum level that is higher than the value set by the caregiver and thus there is a potential danger of the patient seeing too high a value of vacuum level at the body cavity being drained.

Accordingly, it would be advantageous to provide some means of making it easier for the caregiver to set or reset a level of vacuum on a vacuum regulator with an enhanced, predictable accuracy by some system that would ensure that the vacuum line leading to the patient upstream of the vacuum regulator is positively occluded and therefore that there is truly a "no flow" condition in the vacuum system so that the observed reading on the vacuum gauge is accurate. It would be even more advantageous for that means of occluding the patient line to be at a convenient location with respect to the vacuum regulator and vacuum gauge so that the caregiver can carry out all of the necessary operations at the same time, at the same location and not be distracted by trying to carry out multiple functions at diverse locations.

SUMMARY OF THE INVENTION

Accordingly, the present invention relates to a method and system to carry out the establishing and/or resetting of a vacuum level to a patient in a line withdrawing fluids from that patient by providing a positive means of occluding the patient line upstream of the vacuum regulator. As used herein, the convention will be employed that follows the flow in the vacuum line, that is, the source of vacuum will be a downstream location and the patient cavity at an upstream location and the terms upstream and downstream will be used with reference to the flow of fluid in the direction from the patient toward the source of vacuum.

Thus, in accordance with the present invention, a flow switch is provided that causes a positive occluding of the vacuum line upstream of the vacuum regulator so that the caregiver can simply activate the switch and be assured that the vacuum line has been fully occluded and the caregiver can thereafter turn full attention to the setting of the vacuum regulator and the visual monitoring of the vacuum gauge.

In a preferred embodiment, the flow switch that can be activated by the caregiver to occlude the vacuum line is in close proximity to the vacuum regulator itself and can even be incorporated as a component of the vacuum regulator so as to be affixed to or incorporated into the same enclosure as the vacuum regulator.

In a more preferred embodiment a combination product is provided, a vacuum regulator/switch that basically combines, in one device, the function of the normal vacuum regulator with the function of a flow switch. In such combination device, the normal or conventional vacuum regulator is adjusted by the rotation of an actuator having a knob and the occluding switch is constructed to be integral with the rotatable actuator so that the caregiver can simply push the actuator knob inwardly along the z axis to fully occlude the patient vacuum line and thereafter, while displaced inwardly, rotate the actuator knob to adjust the level of the vacuum by means of the normal function of the vacuum regulator while observing the vacuum gauge that is provided in the same enclosure. Thus, this embodiment is most convenient and the caregiver can, with one hand, both occlude the vacuum line to the patient and adjust the level of vacuum simultaneously and with the facility of being able to readily observe the vacuum gauge to assure that the vacuum level established to the patient is accurate.

As will be seen, one of the features of a preferred embodiment is that the caregiver cannot change the level of the vacuum used in withdrawing the fluids from a patient without occluding the vacuum line, that is, the flow switch is interconnected with the vacuum regulator such that the system is safe and the caregiver must engage the flow switch to occlude the vacuum line before the level of vacuum can be changed by any manipulation of the vacuum regulator such that no flow conditions must be present for that caregiver to reset the level of vacuum to a desired level.

Additional features and advantages of the invention will become apparent to those skilled in the art upon consideration of the following detailed description of preferred embodiments exemplifying the best mode of carrying out the invention.

DETAILED DESCRIPTION OF THE INVENTION

Figure 1:
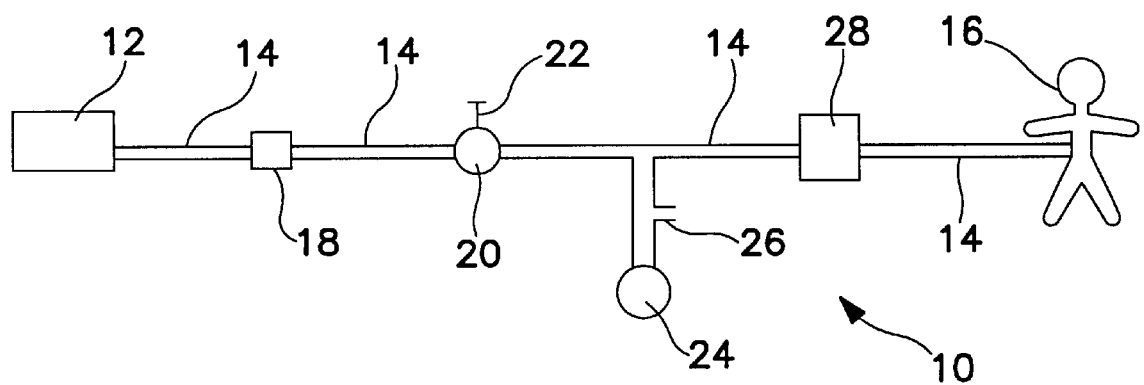
FIG. 1 is a schematic view of a vacuum system constructed in accordance with the present invention.

Turning now to FIG. 1, there is shown a schematic view of vacuum system 10 constructed in accordance with the present invention and where the vacuum system 10 includes, or is adapted to be connected to, a source of vacuum shown as vacuum source 12. As stated, in most hospitals today there is normally provided a pipeline supply of vacuum that is piped to various rooms throughout the hospital and which vacuum is created by means of a centrally located vacuum pump or pumps to maintain the supply of vacuum. As such, in each room so provided, the attending caregiver only needs to plug in the various vacuum utilization equipment to be used in the drainage of a patient cavity, or other purpose, and be able to fully utilize that source of vacuum.

A vacuum line 14, therefore, is used to communicate between that vacuum source 12 and a patient 16 to carry out whatever treatment is needed at that patient 16. In practice, the vacuum line 14 may comprise a plurality of individual vacuum lines, in series communication with each other, however, the principle is that the vacuum source 12 is communicated to the patient 16 through the vacuum line 14 so that vacuum is available at the very end of the vacuum line 14 to communicate with the body cavity of the patient 16. The actual device that is used to enter and communicate with the patient cavity may be a cannula, catheter, drainage tube, naso-gastric tube or the like that actually enters the body cavity of the patient 16.

It is also conventional in such vacuum systems 10 currently used in hospitals to include a main vacuum switch 18 downstream of any of the equipment or apparatus to be used in the hospital room so that the source of vacuum can be connected and disconnected from the vacuum source 12. Thus, a main vacuum switch 18 is basically an on-off valve or switch that is activated to allow communication or cut off that communication between the vacuum source 12 and the equipment associated with the supplying of that vacuum to the patient 16.

In addition, there is normally provided a vacuum regulator 20 that is used to regulate or set the vacuum level that reaches the patient 16 and that vacuum regulator is adjusted by means of an actuator operated by a knob 22 that can be manually rotated by the caregiver to set the level of vacuum to the desired level for the particular patient 16 and/or to suit the particular apparatus used with the patient 16.

Further, there is normally provided a vacuum gauge 24 that enables the caregiver to have a visual perception of the level of the vacuum that is being applied to the patient 16 and the vacuum gauge 24 is located upstream of the vacuum regulator so that it reads the level of vacuum at the upstream side of the vacuum regulator 20, that is, the side of the vacuum regulator 16 where the vacuum level is being applied to the patient 16. A bleed orifice 26 is also provided in vacuum line to the vacuum gauge 24 in order for the vacuum gauge 24 to properly and accurately read the level of that vacuum to the patient 16.

Thus, as can now be seen, the various components described to this point are all conventional components used in hospital vacuum systems and allow a caregiver to set and thereafter adjust the level of the vacuum to the patient 16 by simply rotating the knob 22 while, at the same time, observing the vacuum gauge 24 so that the caregiver can visually ascertain that level of vacuum as the vacuum regulator 20 is manipulated by the caregiver.

As a new component, however to that conventional vacuum system of FIG. 1, there is a positive flow switch 28 that is located in the vacuum line 14 upstream with respect to the vacuum regulator 20 and the vacuum gauge 24. The positive flow switch 28 can be accessed by the caregiver at the upstream side of the vacuum regulator 20 and the vacuum gauge 24 to provide a positive shut off of the vacuum line 14 to the patient 16 and to achieve a no flow condition in the vacuum regulator 20 and the vacuum gauge 24.

By the term positive flow switch, it is meant that the switch can provide a sure and positive occlusion of the vacuum line 14 so that the caregiver, by activating the positive flow switch 28, will be assured that the vacuum line 14 is totally occluded and not allow a leak in the vacuum line 14 that would allow any flow through the vacuum regulator 20. Such switches are readily available on the commercial market by a variety of companies. It is preferred that the positive flow switch 28 be of the type that necessitates the caregiver to maintain some positive pressure on the switch to occlude the vacuum line 14 as opposed to a switch that can remain activated or closed with the users pressure removed. In that manner, the caregiver cannot inadvertently leave the switch in the closed position and the switch will automatically return to the open position when the caregiver has completed the setting of the desired vacuum level to the patient 16 and is no longer attending to the vacuum system 10.

Figure 2:
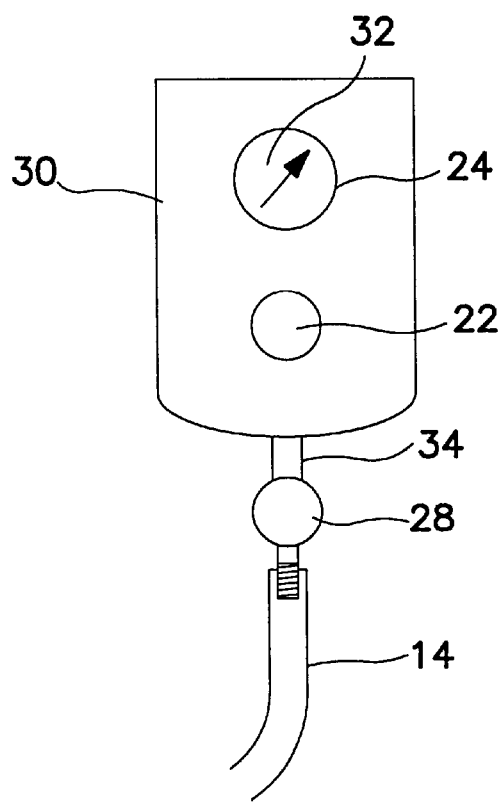
FIG. 2 is a front view of one embodiment of the present invention.

Turning now to FIG. 2, there is shown a front view of a vacuum system constructed in accordance with the present invention. In the FIG. 2 embodiment, the vacuum regulator and the vacuum gauge are both contained within a common enclosure 30 such that the rotatable knob 22 that is used to adjust the vacuum regulator and the face 32 of the vacuum gauge are both accessible to the caregiver to control the setting of the level of the vacuum that is present at the vacuum line 14 that connects to the patient cavity to be drained.

As can be seen, in this embodiment the positive flow switch 28 is firmly affixed to the enclosure 30 by means of a stub 34 so that the caregiver has the convenience of having the positive flow switch 28 right at the same location of the vacuum regulator 20 and the vacuum gauge 24 (FIG. 1) and enables the caregiver to activate the positive flow switch 28 while simultaneously rotating the knob 22 to correctly set the desired vacuum level to be applied to the patient through the vacuum line 14. Thus, there is an added convenience achieved by the firm affixation of the positive flow switch 28 adjacent to or juxtaposed in close proximity to that enclosure 30 containing the vacuum gauge 24 and the vacuum regulator 20.

Figure 3:
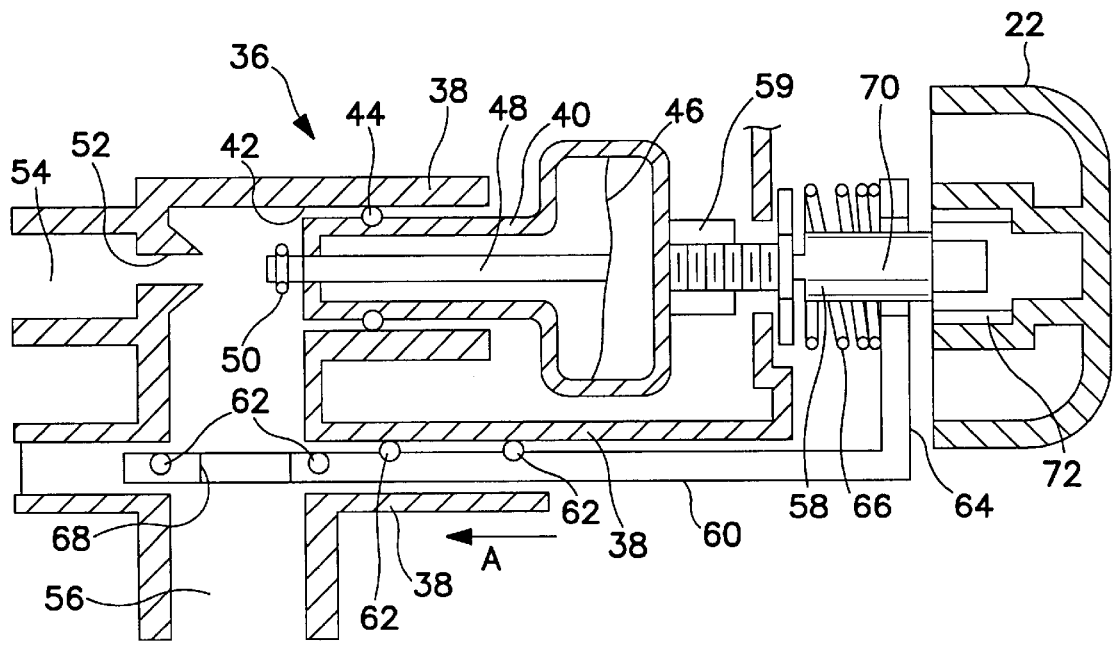
FIG. 3 is a schematic, partial side view of a combination vacuum regulator/flow switch constructed in accordance with the present invention with a flow switch in the open position allowing flow through a vacuum line.
Figure 4:
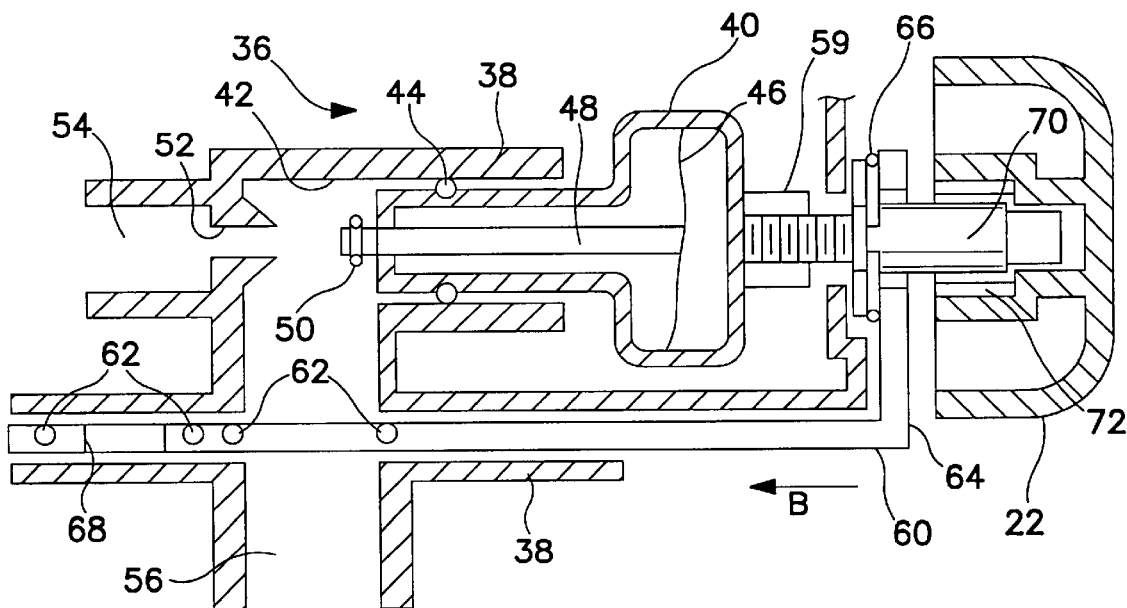
FIG. 4 is a schematic, partial side view of the embodiment of FIG. 3 with the flow switch in its closed position occluding the vacuum line.

Turning now to FIGS. 3 and 4, there are shown, partial side cross sectional views of a vacuum regulator/flow switch 36 that is a combination of a vacuum regulator to control the level of vacuum to a patient and a flow switch that that can be activated by a caregiver to shut off any flow through the vacuum regulator and, as shown, in FIG. 3, the flow switch is in the open position allowing flow through the regulator while in FIG. 4, the flow switch is in the closed position where there is no flow allowed through the regulator.

Accordingly, in FIGS. 3 and 4, there is a housing 38 that encloses the various components to be described herein as well as to locate and position those components with respect to each other. In particular, and which is conventional with vacuum regulators, there is a regulator module 40 that is movably retained within an opening 42 formed in the housing 38 such that the regulator module 40 can move axially within the opening 42 and is sealed therein by means of an O-ring 44. Within the regulator module 40 is commonly provided a diaphragm 46 affixed to a valve stem 48 extending therefrom and also having an O-ring 50 at the distal end thereof.

The distal end of the valve stem 48 and the O-ring 50 form a valve arrangement in cooperation with a narrow aperture 52, also formed in the housing 38 and which leads into the outlet port 54. The outlet port 54 is basically the downstream end of the vacuum regulator part of the vacuum regulator/flow switch 36 and is adapted to be connected to the vacuum source 12 (FIG. 1). An inlet port 56 is also formed in the housing 38 and is adapted to be connected to the upstream vacuum line that ultimately leads to the particular patient cavity or other end use of the vacuum system.

As still another conventional component of the vacuum regulator, there is an actuator 58 that is adapted to be rotated in order to change the axial position of the regulator module 40 with respect to the narrow aperture 52 in order to effect a change in the vacuum level at the inlet port 56. That change in axial position is conventionally carried out by a internally threaded boss 59 formed on the regulator module 40 into which the actuator 58 is threadedly engaged so that the rotational movement of the actuator 58 will axially move the regulator module 40.

To this point, the vacuum regulator function or portion of the vacuum regulator/flow switch 36 is basically the normal components of a conventional vacuum regulator, however, in accordance with the present invention, there is a flow switch added to the normal vacuum regulator function. To that end, there is a switch actuator 60 that is mounted to the housing 38 so as to be axially movable with respect to that housing 38. As can be seen, the switch actuator 60 is movable in the direction of the arrow A of FIG. 3 and the switch actuator is sealed to the housing by means of one or more O-rings 62.

The switch actuator 60 includes an inwardly extending flange 64 that is located between the knob 22 and the outer surface of the housing 38 and has an opening 68 that, in FIG. 3, is aligned with the inlet port 56 so that flow can pass through the vacuum regulator/flow switch 36 from the inlet port 56 through to the outlet port 54, depending, of course, on the position of regulator module 40. The knob 22 itself is loosely retained on to the flange 64 or to the actuator 58 by means, not shown. A spring 66 is located between the flange 64 and the housing 38 such that the switch actuator 60 is continually biased toward its outer or switch open position of FIG. 3. As can be seen in FIG. 4, however, the switch actuator 60 has been moved in the direction of the arrow B, against the bias of the spring 66 to a closed position or a "no flow" position where the opening 68 of the switch actuator 60 is not aligned with the inlet port 56 and any flow through the inlet port 56 is prevented.

In the operation of the switch actuator 60, the outer end of the regulator actuator 58 is a splined shaft 70 and which meshes with a corresponding female splined hole 72 in the knob 22 such that the knob 22 can move axially along the splined shaft 70. In FIG. 4, therefore, the knob 22 has been moved toward the housing 38 against the spring bias to the closed position by the knob 22 being pushed inwardly by the caregiver whereupon the splined connection between the knob 22 and the regulator actuator 58 engages to allow the caregiver to simply rotate the knob 22 to operate the regulator function of the vacuum regulator/flow switch 36 to set the vacuum level to the desired amount while, at the same time, the inlet port 56 has been occluded by the switch actuator 60 shutting off the vacuum line at the inlet port 56 such that the regulator function is at "no flow" conditions.

Thus, the caregiver can simply look at the vacuum gauge (FIG. 2) and set the vacuum regulator to the desired level of vacuum to the patient with assurance that such setting is being done at "no flow" conditions and that the setting will result in an accurate setting of the level of vacuum to the patient. When the desired vacuum setting has been made by the caregiver, the caregiver merely releases the knob 22 and the knob 22 along with the switch actuator 60 will return, by means of the outward bias of spring 66, to the switch open position as shown in FIG. 3.

According, as a quick summary, when the caregiver wants to establish or change a setting of the level of vacuum to a patient, that caregiver simply pushes inwardly on the knob 22, thereby engaging the splined shaft 70 that is formed on the end of the regulator actuator 58. At the same time, as the splined shaft 70 is engaged, the switch actuator is moved axially in the direction of the arrow A of FIG. 3 to the closed or "no flow" position of FIG. 4 where the inlet port 56 of the vacuum regulator/switch 36 is therefore automatically occluded.

Therefore, in the "no flow" position of FIG. 4, the caregiver can simply then rotate the regulator actuator 58 to carry out the normal function of a vacuum regulator to set the desired level of vacuum to the patient while being assured that the vacuum system is at the "no flow" condition and the set level of vacuum will be the maximum vacuum that can reach the patient. When that desired setting had been reached, the caregiver releases the knob 22 and that knob moves by the bias of spring 66 in the direction of the arrow B of FIG. 4 back to the open switch condition of FIG. 3 and the knob 22 becomes again disengaged from the splined shaft 70. Thus, in one simple operation, the caregiver can establish or change the setting of the vacuum to the patient and still be assured that any such setting has been accomplished under no flow conditions and further be assured that the set vacuum is then acting upon the patient.

Figure 5:
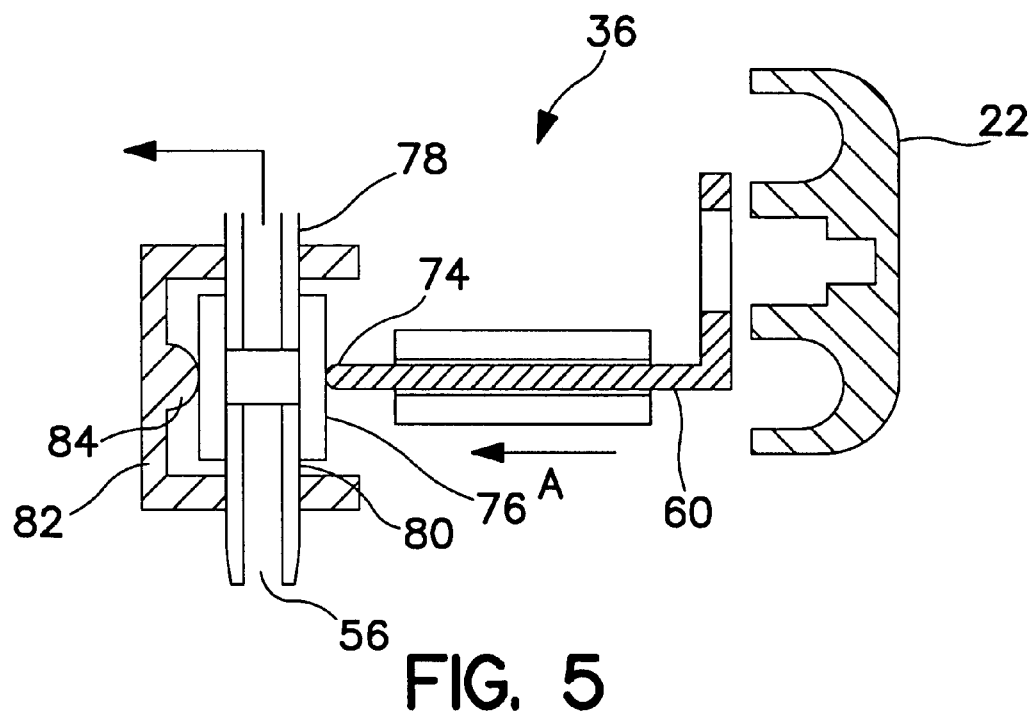
FIG. 5 is a schematic side view of a further embodiment of the present invention with a flow switch in the open position allowing flow through a vacuum line.
Figure 6:
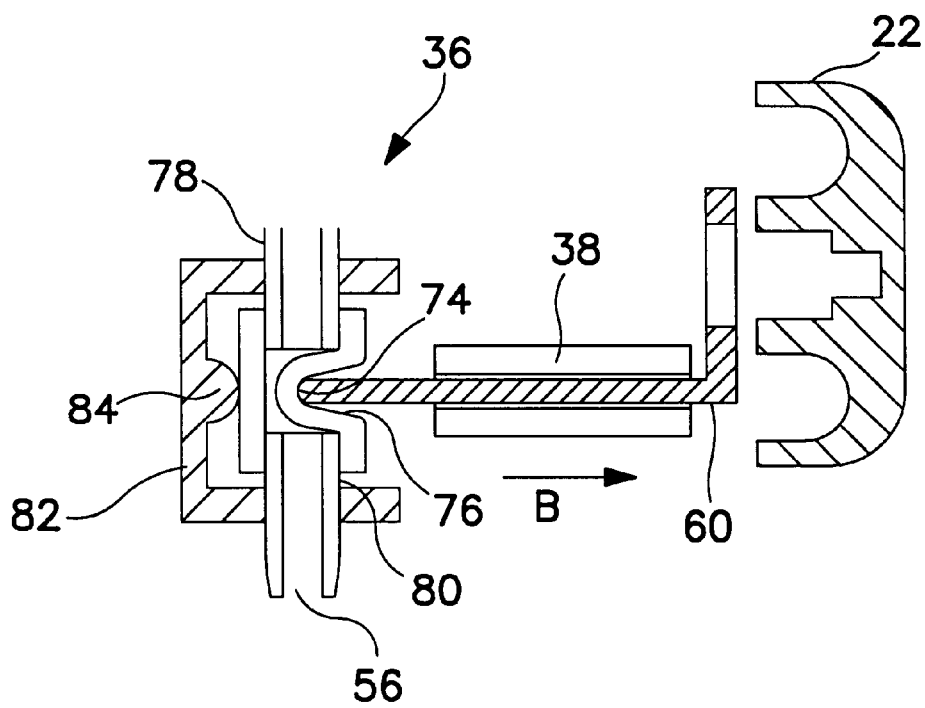
FIG. 6 is a schematic side view of the embodiment of FIG. 5 with a flow switch in the closed position occluding the vacuum line.

Turning now to FIGS. 5 and 6, there is shown a partial side sectional view of a further embodiment of the present invention with a different design of a vacuum flow switch and to which like numbers have been used on comparable parts as previously described with respect to FIGS. 3 and 4. In this embodiment, the switch actuator 60 is in the shape of a rod having a distal tapered end 74. At or adjacent the inlet port 56, there is a flexible tubing 76 spanning a distance between two fittings 78, 80 formed within a frame member 82. The fittings 78, 80 as well as the flexible tubing 76 are a part of the vacuum line that communicates between the vacuum source 12 and the patient 16 (FIG. 1). There is a protrusion 84 formed on the frame member 82 and, as can be seen, as the switch actuator 60 is pushed in the direction of the arrow A shown in the open position of FIG. 5 to the "no flow" position of FIG. 6, the flexible tubing 76 is sandwiched between the tapered end 74 of the switch actuator 60 and the protrusion 84 to close that flexible tubing 76 and thus occlude the inlet port 56.

Again, as with the FIGS. 3 and 4 embodiment, therefore, the caregiver can simply push in the knob 22 and automatically bring about the occlusion of the inlet port 56 of the vacuum regulator/switch 36. Upon release of the knob 22, the knob 22 will spring back, in the direction of the arrow B of FIG. 6 to return to the open or flow position of FIG. 5.

The further components required to carry out the regulator function in the FIGS. 5 and 6 embodiment are the same as in the FIGS. 3 and 4 embodiment and are therefore not shown in the latter embodiment, it being evident as to the means of combining the flow switch function of the FIGS. 5 and 6 embodiment with the regulator function as shown and described in FIGS. 3 and 4.

Figure 7:
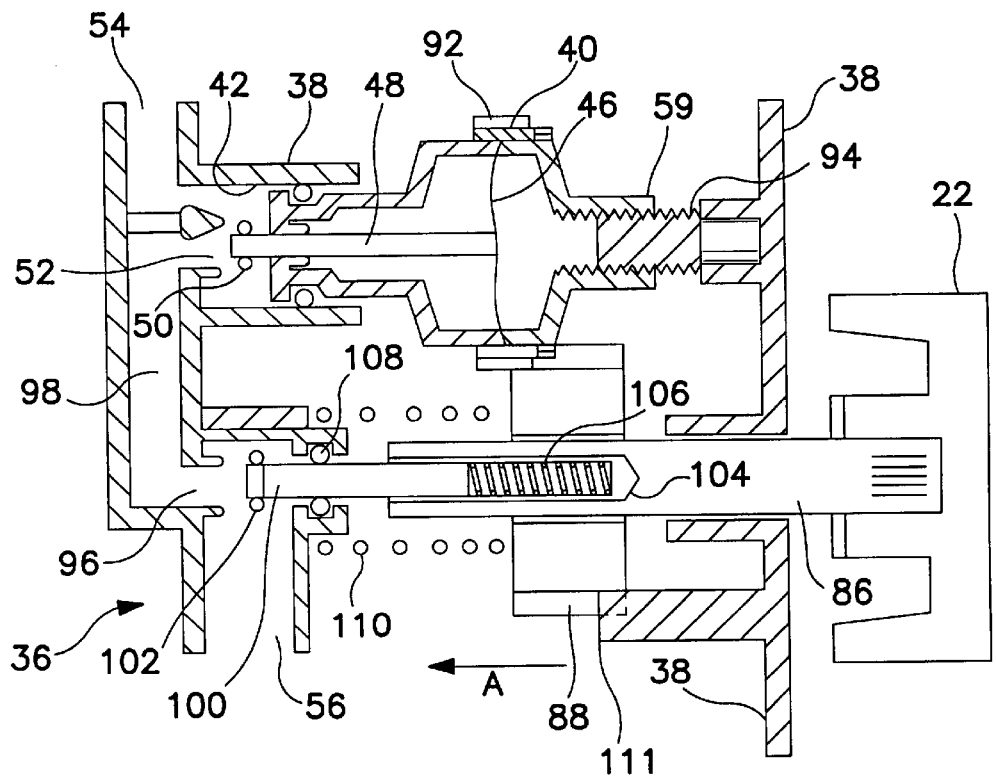
FIG. 7 is a schematic side view of a still further embodiment of the present invention with a flow switch in the open position allowing flow through a vacuum line.
Figure 8:
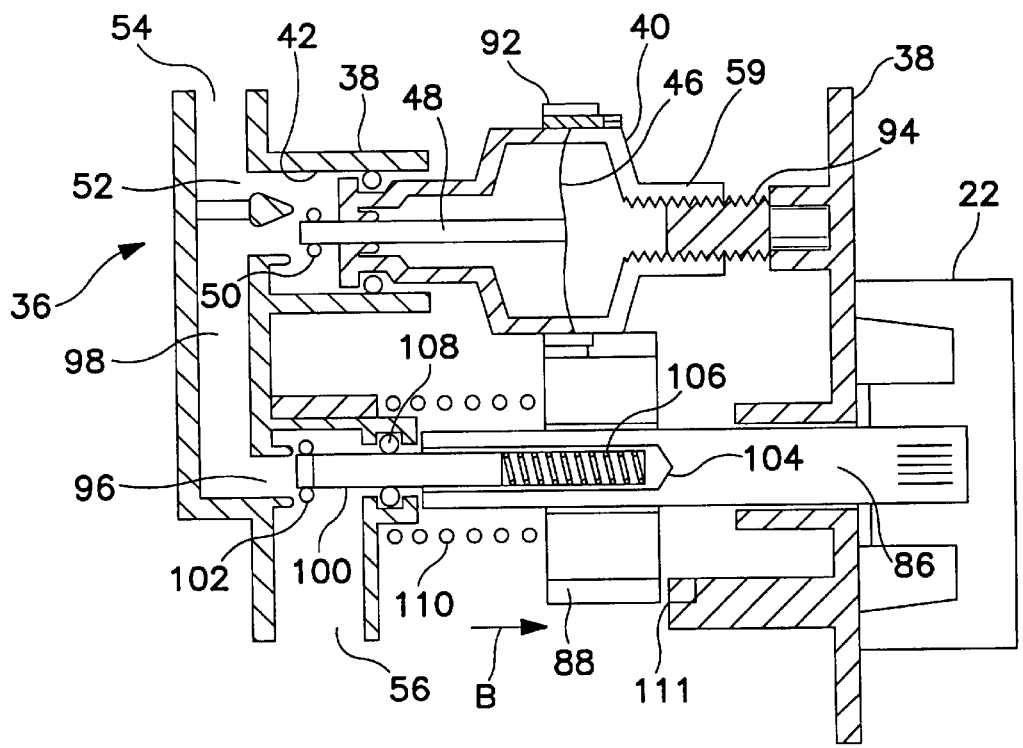
FIG. 8 is a schematic side view of the embodiment of FIG. 7 with a flow switch in the closed position occluding the vacuum line

Finally in FIGS. 7 and 8, there are shown partial side cross sectional schematic views of a still further embodiment of a vacuum regulator/flow switch 36 and, again, like numbers have been applied where the components or parts are basically the same as described with respect to the prior embodiments. In FIGS. 7 and 8, however, there is a separate idler shaft 86 having an axis that is displaced away from the normal axial alignment with the regulator module 40 and the knob 22 is permanently affixed to the outer end of that idler shaft 86. Again, the idler shaft 86 is rotatably affixed within the housing 38 and is adapted to move axially in the direction of the arrow A of FIG. 7 to be moved from the open switch position of FIG. 7 to the closed, no flow position of FIG. 8. As can also be seen, there is an idler gear 88 affixed to the idler shaft 86.

The idler gear 88 is adapted to intermesh with mating configured gear teeth 92 formed on the exterior of the regulator module 40 that is, as with the prior embodiments, mounted so as to allow axial movement to effect the control of the vacuum level. In this case, however, the regulator module 40 is also rotatably mounted in the housing 38 and a fixed, threaded shaft 94 that is engaged to the internally threaded boss 59 formed on the regulator module 40. Thus, since the fixed, threaded shaft 94 does not rotate, as the regulator module 40 itself is rotated, the regulator module 40 moves axially in accordance with the pitch of the meshing gears between the internally threaded boss 59 and the fixed, threaded shaft 94 to control the position of the valve stem 48 with respect to the narrow aperture 52 to control the level of the vacuum at the inlet port 56.

The knob 22 of this embodiment is therefore displaced with respect to the normal location of the regulator module 40 in the prior embodiments and, as will be seen, directly operates the vacuum switch function of the vacuum regulator/flow switch 36. In this embodiment, there is a restricted orifice 96 just downstream from the inlet port 56 and which communicates with an enclosed passageway 98 that leads into the opening 42 of the regulator portion of the vacuum regulator/flow switch 36.

Thus, extending from the inner end of the idler shaft 86 is a valve shaft 100 that is adapted to move axially, along with the axial movement of the idler shaft 86, and, with that movement, the valve shaft 100 can move from an open position where the valve shaft 100 is displaced from the restricted orifice 96 as shown in FIG. 7 in the direction of the arrow A into engagement blocking the restricted orifice 96 in the switch closed or "no flow" position of FIG. 8. An O-ring 102 is located at the extending end of the valve shaft 100 in order to provide a good seal to make sure that the restricted orifice 96 is fully occluded. In order to allow a certain amount of play in the occluding and opening of the restricted orifice 96 by means of the O-ring 102, the valve shaft 100 is preferable biased within a cavity 104 formed in the idler shaft 86 by means of a spring 106. In addition, the valve shaft 100 is sealed within the housing 38 by means of an O-ring 108.

While the knob 22 can thus be moved in the direction of the arrow A of FIG. 7, acting against that movement is a bias provided by a spring 110 located intermediate the idler gear 88 and the housing 38 so that the movement of the knob 22 and, of course, the idler shaft 86 in the direction of the arrow A against the spring bias and upon the release of any force on the knob 22 by the caregiver, the idle gear 88 will move in the direction of the arrow B and the idler gear 88 will automatically engage the stop pawl 111 and thereby stopping the knob 22 and the idler shaft 86 from rotating. As such, the idler gear 88 and the mating configured gear teeth 92 are always intermeshed even during the axial movement of the idler shaft 86 between its positions shown in FIGS. 7 and 8, however, when the idler shaft 86 is in the open position of FIG. 7, the knob 22 is prevented from rotating by the stop pawl 111 engaging the idler gear 88 so as to prevent the knob 22 from even being rotated by the user unless the vacuum regulator/flow switch 36 is in the closed position and thus in the no flow condition.

Accordingly, as a brief summary of the operation of the embodiment of FIGS. 7 and 8, when the caregiver desires to establish, or alter, the setting of the level of the vacuum to a patient, as with the prior embodiments, the caregiver can push inwardly on the knob 22 to move it laterally inwardly and which, at the same time, moves the valve shaft 100 from the open position of FIG. 7 to the closed, "no flow" position of FIG. 8 where the O-ring 102 occludes the restricted orifice 96 and prevents flow through the vacuum regulator/switch 36.

Simultaneously, therewith, as the idler shaft 86 is moved in the direction of the arrow A of FIG. 7, the idler gear 88 is caused to disengage with the stop pawl 111 formed on the interior surface of the housing 38. Thus, when the idler shaft 86 has reached the position of FIG. 8, the vacuum switch has been closed, that is, the restricted orifice 96 has been fully occluded, so that there is no flow at the inlet port 56. At that point, the knob 22 can simply be rotated by the caregiver and the idler gear 88 will also rotate the regulator module 40 and, by means of the interengagement of the screw thread within the boss 59 and the fixed threaded shaft 94, cause the regulator module 40 to move axially to adjust the vacuum level that can read by the caregiver on the vacuum gauge (not shown in FIG. 7 or 8) to set the desired level of vacuum and be assured that such level of vacuum will be the maximum level that will be seen by the patient.

Again, when the knob 22 is released, the idler gear 88 will return to the FIG. 7 position and the vacuum switch again opened by moving in the direction of the arrow B of FIG. 8 so that the idler gear 88 will become engaged with the stop pawl 111 and be prevented from rotating.

Accordingly, as is now clear with respect to the FIGS. 3–8 embodiments, there is a built in safety factor in that unless the knob 22 is pushed inwardly, the knob 22 is simply fixed with respect to rotation and cannot be rotated by the caregiver to change of the level of the vacuum to the patient since, unless depressed the knob 22 will not be rotatable to affect the regulation of the level of the vacuum to the patient. In other words, knob 22 must be depressed in order to change the level of the vacuum to the patient and thus the caregiver is assured that the vacuum regulator is at "no flow" conditions and the vacuum line occluded or the vacuum level cannot be changed by the caregiver.

Those skilled in the art will readily recognize numerous adaptations and modifications which can be made to the vacuum regulator/switch, vacuum system and method of establishing vacuum of the present invention which will result in an improved system yet all of which will fall within the scope and spirit of the present invention as defined in the following claims. Accordingly, the invention is to be limited only by the following claims and their equivalents.

We claim:

1. A vacuum system adapted to withdraw fluids from a body cavity of a patient, said vacuum system comprising a source of vacuum, a vacuum line providing communication between said source of vacuum and the patient cavity, a vacuum regulator in said vacuum line adapted to be adjusted to establish the level of vacuum to the patient cavity, a vacuum gauge to provide a visual indication of the level of vacuum in said vacuum line, and a flow switch located in said vacuum line upstream of said vacuum regulator, said flow switch being activatable to positively occlude said vacuum line to establish a no flow condition in said vacuum line.

2. A vacuum system as defined in claim 1 wherein said flow switch is activatable between a closed position positively occluding said vacuum line and an open position positively opening said vacuum line and is biased toward said open position.

3. A vacuum system as defined in claim 1 wherein said flow switch is located in close proximity to said vacuum regulator.

4. A vacuum system as defined in claim 2 wherein said flow switch is interconnected to said vacuum regulator such that said vacuum regulator cannot be adjusted unless said flow switch is in said closed position.

5. A vacuum system as defined in claim 1 wherein said vacuum regulator is enclosed with a housing and said flow switch is affixed to said housing.

6. A combination vacuum regulator and flow switch, said combination comprising a housing having an outlet adapted to be connected to a source of vacuum, and an inlet adapted to be connected to a vacuum line for introduction into a body cavity of a patient and a passageway therebetween, a vacuum gauge adapted to provide a visual indication of the level of vacuum at said inlet, a vacuum regulator intermediate said inlet and said outlet, said vacuum regulator having an actuator that is rotatable to adjust the level of vacuum at said inlet, said actuator having an open position and a closed position occluding said inlet, said actuator being movable in an axial direction to said closed position to prevent the flow of fluid through said vacuum regulator, said actuator having an opening formed therein, said opening being aligned with said inlet when said actuator is in said open position and said opening being displaced from said inlet when said actuator is in said closed position.

7. A combination vacuum regulator and flow switch as defined in claim 6 wherein said actuator is biased toward said open position.

8. A combination vacuum regulator and flow switch, said combination comprising a housing having an outlet adapted to be connected to a source of vacuum, and an inlet adapted to be connected to a vacuum line for introduction into a body cavity of a patient and a passageway therebetween, a vacuum gauge adapted to provide a visual indication of the level of vacuum at said inlet, a vacuum regulator intermediate said inlet and said outlet, wherein said vacuum regulator has a rotatable element having an axis of rotation to adjust the level of vacuum at said inlet, said vacuum regulator having an actuator that is rotatable about an axis that is displaced with respect to the axis of said rotatable element of said vacuum regulator, said actuator further being movable in an axial direction to occlude said inlet to prevent the flow of fluid through said vacuum regulator.

9. A combination vacuum regulator and flow switch as defined in claim 8 wherein said actuator and said rotatable element of said vacuum regulator are interengaged.

10. A combination vacuum regulator and flow switch as defined in claim 8 wherein said interengagement between said actuator and said rotatable element comprises meshing gears.

11. A combination vacuum regulator and flow switch as defined in claim 8 wherein said actuator has an open position and a closed position occluding said inlet, and wherein said rotatable element is only rotatable to adjust the level of vacuum at said inlet when said actuator is in said closed position occluding said inlet.

12. A combination vacuum regulator and flow switch as defined in claim 11 wherein said actuator is biased toward said open position.

13. A combination vacuum regulator and flow switch as defined in claim 11 wherein said actuator is prevented for rotating when said actuator is in said open position.

14. A method of establishing a level of vacuum to a patient, said method comprising the steps of:

providing a source of vacuum, providing a vacuum line to communicate that source of vacuum to an internal cavity of a patient, providing a vacuum gauge to visually ascertain the level of vacuum in the vacuum line, providing a vacuum regulator to adjust the level of vacuum in the vacuum line, providing a flow switch in a location upstream of the vacuum regulator and the vacuum gauge that is operable to fully occlude the flow with the vacuum line, activating the flow switch to achieve a no flow condition within the vacuum line while simultaneously adjusting the level of vacuum in the vacuum line by the vacuum regulator.

15. A method of establishing a level of vacuum to a patient as defined in claim 14 wherein said step of providing a flow switch comprises providing a flow switch located in close proximity to the vacuum regulator.

16. A method of establishing a level of vacuum to a patient as defined in claim 15 further including the step of interengaging the flow switch and the vacuum regulator to prevent the adjusting of the vacuum regulator unless the flow switch has been activated to achieve a no flow condition.

* * * * *